(12) United States Patent
Komissarov et al.

(10) Patent No.: US 10,175,255 B2
(45) Date of Patent: Jan. 8, 2019

(54) FIBRINOLYTIC POTENTIAL: A TEST OF PLEURAL FLUID TO PREDICT OUTCOMES AND GUIDE DOSING IN FIBRINOLYTIC THERAPY

(71) Applicant: Board of Regents, The University of Texas System, Austin, TX (US)

(72) Inventors: Andrey A. Komissarov, Lindale, TX (US); Galina Florova, Beaverton, OR (US); Steven Idell, Tyler, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 59 days.

(21) Appl. No.: 15/086,623

(22) Filed: Mar. 31, 2016

(65) Prior Publication Data

US 2016/0291043 A1    Oct. 6, 2016

Related U.S. Application Data

(60) Provisional application No. 62/141,032, filed on Mar. 31, 2015.

(51) Int. Cl.
*G01N 33/50*      (2006.01)
*G01N 33/86*      (2006.01)
*C12N 11/00*      (2006.01)

(52) U.S. Cl.
CPC .................. *G01N 33/86* (2013.01)

(58) Field of Classification Search
CPC .............. A61K 2300/00; A61K 35/16; A61K 38/1722; A61K 45/06; A61K 2039/505; A61K 35/19; A61K 35/28; A61K 38/1841; A61K 38/19; A61K 38/191; A61K 38/4886; A61K 39/3955; A61K 31/713; A61K 2039/545; A61K 31/454; A61K 38/00; A61K 49/0002; A61K 49/0032; A61K 49/0043; A61K 49/0056; C07K 7/06; C07K 14/78; C07K 5/1016; C07K 7/08; C07K 7/56; C07K 7/64; G01N 33/86; G01N 2500/04
See application file for complete search history.

(56) References Cited

U.S. PATENT DOCUMENTS

| 6,984,373 B2 * | 1/2006 | Wescott ............. A61K 49/0002 424/1.69 |
| 2003/0143158 A1 * | 7/2003 | Wescott ............. A61K 49/0002 424/1.69 |
| 2005/0261472 A1 * | 11/2005 | Wescott ............. A61K 49/0032 530/328 |
| 2008/0268483 A1 | 10/2008 | Goldenberg et al. |
| 2013/0006526 A1 | 3/2013 | Grunzke et al. |

OTHER PUBLICATIONS

AA Komissarov et al., Effects of Extracellular DNA on Plasminogen Activation and Fibrinolysis, J. Biol. Chem. 286:41949-41962 (2011).
S. Karandashova et al., Intrapleural Adenoviral Delivery of Human Plasminogen Activator Inhibitor-1 Exacerbates Tetracycline-Induced Pleural Injury in Rabbit, Am.J.Respir.Cell Mol.Biol. 48:44-52 (2013).
AA Komissarov, AA et al., Active α-macroglobulin is a reservoir for urokinase after fibrinolytic therapy in rabbits with tetracycline-induced pleural injury and in human pleural fluids, Am.J.Physiol Lung Cell Mol.Physiol 305:L682-92 (Aug. 30, 2013)).
G. Florova et al., Targeting of Plasminogen Activator Inhibitor 1 Improves Fibrinolytic Therapy for tetracycline-Induced Pleural Injury in Rabbits, Am J Respir Cell Mol Biol 52(4) 429-437, Apr. 2015.
AA Komissarov et al., The time course of resolution of adhesions during fibrinolytic therapy in tetracycline-induced pleural injury in rabbits, Am J Physiol Lung Cell Mol Physiol 309: L562-L572, 2015.
AA. Komissarov et al., Dose dependency of outcomes of intrapleural fibrinolytic therapy in new *rabbit empyema models , Am J Physiol Lung Cell Mol Physiol 311: L389-L399, 2016. First published Jun. 24, 2016.
S. Idell et al., Abnormalities of Pathways of Fibrin Turnover in the Human Pleural Space, Amer Rev Respir Dis 144:187-194 (1991).
H.A. Chapman, Disorders of lung matrix remodeling, J. Clin. Invest. 113:148-157 (2004).
G. Florova, et al., DNA Dramatically Potentiates Activation off Plasminogen by Tissue Type Plasminogen Activator Am. J. Respir. Crit. Care Med. 181:Abstr 6824 (2010).
S. Idell, The pathogenesis of pleural space loculation and fibrosis. Curr. Opin. Pulm. Med. 14:310-315 (2008).
S. Idell, S., Coagulation, fibrinolysis, and fibrin deposition in acute lung injury, Crit. Care Med. 31:S213-S220 (2003).
Wu, JH et al., Fluorogenic fibrinogen and fibrin facilitate macromolecular assembly and dynamic assay of picomolar levels of plasminogen activators under well mixed conditions. Thromb. Haemost. 74:711-17, (1995).
Rahman, NM et al., Intrapleural use of tissue plasminogen activator and DNase in pleural infection N. Engl. J. Med. 365:518-526 (2011).

* cited by examiner

*Primary Examiner* — Deborah K Ware
(74) *Attorney, Agent, or Firm* — Browdy and Neimark, PLLC (57) ABSTRACT

An assay that informs precision-based intrapleural fibrinolytic therapy (IPFT) is disclosed. Provided is a simple assay based on measurement of the Fibrinolytic Potential (FP)—total fibrinolytic activity in pleural fluid when plasminogen activator inhibitors (PAIs) are neutralized and endogenous plasminogen (PLG) is activated. The assay is used to determine FP in baseline pleural fluids of patients undergoing IPFT with agents such as tPA or scuPA to determine the dose and dose intervals for the particular patient. Pleural fluids are also collected after IPFT to confirm that intrapleural fibrinolysis is inhibited and endogenous PLG accumulates in the pleural fluid. Inhibition of intrapleural fibrinolysis in combination with its increase after supplementation of pleural fluid with a plasminogen activator indicates whether or not the subject should be treated with more or higher doses of an IPFT drug.

34 Claims, 2 Drawing Sheets
(1 of 2 Drawing Sheet(s) Filed in Color)

FIBRINOLYTIC POTENTIAL: A TEST OF PLEURAL FLUID TO PREDICT OUTCOMES AND GUIDE DOSING IN FIBRINOLYTIC THERAPY

STATEMENT OF RIGHTS TO INVENTIONS MADE UNDER FEDERALLY SPONSORED RESEARCH

This invention was funded in part by grants NIH P50 107186 (CADET 1) and CADET II:1UH2HL123585-01. from the National Heart, Lung and Blood Institute, National Institutes of Health, which provides to the United States government certain rights in this invention.

BACKGROUND OF THE INVENTION

Field of the Invention

The invention in the field of biochemistry and medicine relates to a method testing pleural fluid samples in conjunction with fibrinolytic therapy.

Description of the Background Art

Approximately 65,000 patients in the United States alone develop empyema (EMP) or related complicated parapneumonic pleural effusions annually. The incidence of EMP is increasing worldwide. EMP is associated with serious morbidity, a mortality of about 20%, and patient care costs of roughly $500 million per year (Burgos, J et al. *Curr. Opin. Pulm. Med.* 19:350-356 (2013); Grijalva, C G et al. *Thorax* 66:663-668 (23011); Hendrickson, D J et al. *Pediatr. Infect. Dis. J.* 27:1030-1032 (2008); Maskell, N A et al. *N. Engl. J. Med.* 352:865-874 (2005); Bender, J M et al. *Emerg. Infect. Dis.* 15:44-48 (2009))

Intrapleural fibrinolytic therapy (IPFT) has been used for over 60 years to expedite pleural drainage and prevent lung restriction, but its efficacy and safety profile, especially in adults, remains uncertain. Bleeding occurs in up to 15% of patients. Current IPFT protocols use empirically dosed, off-label interventions and reflect rudimentary knowledge about the regulation of IPFT in EMP and its pathogenesis (Krishnan, S et al., *Chest* 112:1579-83 (1997); Kornecki, A et al. *J. Pediatr. Surg.* 32:1473-15. (1997); Handman, H. P et al. *Pediatr. Infect. Dis. J.* 12:958-59 (1993); de Benedictis, F M et al. *Pediatr. Pulmonol.* 29:438-42 (2000); Barbato, A et al. *Pediatr. Pulmonol.* 35:50-65 (2003); Stringel, G et al. *J. Pediatr. Surg.* 29:1539-40 (1994); Sonnappa, S et al. *Am. J. Respir. Crit Care Med.* 174:221-27 (2006); Sonnappa, S et al. *Paediatr. Respir. Rev.* 8:164-70 (2007); Barnes, N P et al. *Pediatr. Pulmonol.* 39:127-34 (2005); Thomson, A H et al. *Thorax.* 57:343-47 (2002); Stefanutti, G et al. *Surgery* 148:589-94 (2010). The present invention is project is designed to address these critical gaps which have slowed the progress in the field and fostered empiric approaches to the use of IPFT Corcoran, J P et al. *Chest* 145:14-17 (2014); Colice, G L and Idell, S *Chest* 145:17-20 (2014); Colice, G L and Idell, S 2014. Response. *Chest* 146:e104-105 (2014)

The present inventors and their colleagues identified and validated active plasminogen activator inhibitor 1 (PAI-1) as a biomarker and therapeutic target for IPFT in pleural injury. Karandashova, S et al. *Am. J. Respir. Cell Mol. Biol.* 48:44-52 (2013); Komissarov, A A et al. *Am. J. Physiol Lung Cell Mol. Physiol* 305:L682-92 (2013)) Three mechanistically different forms of PAI-1 targeted IPFT are effective in reversing tetracycline-induced pleural organization in rabbits. These interventions allow the use much lower doses of fibrinolysin for therapy—up to 8-fold decreased, and otherwise ineffective, doses. This mitigates bleeding risk.

There is no clinically tractable testing currently available to guide delivery of intrapleural fibrinolytic therapy or to predict its outcomes, so that this test advances this medical management problem. The present inventors designed a companion diagnostic test; the Fibrinolytic Potential Assay (FPA), the subject of this application, to monitor outcomes of PAI-1 targeted or other forms of IPFT. This invention prediction of outcomes of intrapleural fibrinolytic therapy, how to dose the intervention and when to give it. No such test is currently available and current fibrinolytic therapy yields unpredictable outcomes as dosing is currently completely empiric, which may compromise efficacy and safety.

SUMMARY OF THE INVENTION

The method of the present invention, the Fibrinolytic Potential Assay (FPA), is based in part on the inventors' discovery that PAI-1 targeted IPFT can effectively clear intrapleural organization in EMP. The FPA is able to predict outcomes of IPFT and therefore, is useful for selecting subjects more likely than others to benefit from such therapy, as well as for establishing optimal dosages and dose regiments. Evaluation of the FPA has been conducted with PAI-1 targeted IPFT in four EMP models for predicting pleural injury outcomes.

Improve the efficacy of IPFT in rabbit EMP using PAI-1 targeted delivery;

Determine the molecular mechanisms governing intrapleural fibrinolysis in EMP and the effects of high levels of extracellular DNA on PAI-1 targeted IPFT;

Select the single most effective PAI-1 targeted IPFT in EMP, develop and further validate the companion FPA test using EMP fluids from the models and patients; and Optimize the structure and co-formulation of novel IPFTs for EMP and evaluate their safety and efficacy.

The inventors use a range of state-of-the-art biochemical, physiologic, tissue analysis and imaging techniques with the FPA, thereby addressing needs that have thus far not been met in diagnosis of EMP and identification and preclinical vetting of new, potentially more effective and safer IPFT candidates that are clinically tractable and improve clinical outcomes.

The present invention provides a basis to predict outcomes and efficacy of different approaches to PAI-1 targeted IPFT, including in two new EMP animal models as well as in patients in need of IPFT. This approach is supported by the present inventors' previous work that enhanced understanding of the mechanisms that govern fibrin turnover in pleural injury.

Specifically, the present invention is directed to an assay method for measuring a mammalian subject's fibrinolytic potential (FP) in a sample of pleural fluid of the mammalian subject, preferably a human, comprising:

(a) incubating the pleural fluid sample with detectably labeled fibrin bound to a solid phase substrate, (b) adding to the sample of (a) an activator of plasminogen (PLG), for example, tPA, uPA or streptokinase; preferably the amount of PLG activator is between about 0.1 µg/ml and 0.5 µg/ml, and (c) measuring fibrinolysis of the labeled fibrin by measuring detectable label released from the labeled bound fibrin, wherein the amount of label released per unit of time or during a preset time is a measure of the subject's FP Preferably, DNA is also bound to the solid phase substrate together with the labeled fibrin.

In the above method, the detectable label is preferably one selected from the group consisting of (a fluorescer or fluorogen, a chromophore or chromogen, a phosphorescer, a chemiluminescer, a bioluminescer, and a radionuclide, more preferably a fluorescer, most preferably, fluorescein which is preferably bound to the fibrin as fluorescein isothiocyanate.

In the above method, the solid phase substrate is preferably a polymer selected from the group consisting polystyrene, polypropylene, polyethylene, dextran, nylon, polyacrylamide, polyvinylidene difluoride, natural cellulose, modified cellulose, nitrocellulose, and agarose. More preferably, the solid phase substrate is in the form of polystyrene or other plastic multiwell plate to which the labeled fibrin is bound.

Also provided is a method of predicting the severity of a pleural disease or condition or selecting an appropriate treatment, including an effective dose or dosing interval of an intrapleural fibrinolytic therapeutic (IPFT) agent in a mammalian subject, preferably a human subject, suffering from a disease or condition in need of the IPFT. This is important because of the potential dangers associated with the administration of unnecessarily high doses of the drugs used in IPFT. The method comprises:

(a) performing the assay method of claim 1 on a pleural fluid sample from the subject to determine the FP of the subject and obtaining a standard curve preferably defined over a range of from 0-10 arbitrary units (A.U.) of fibrinolytic activity;

(b) comparing the FP of the subject to the standard curve, taking into account the subject's clinical parameters, preferably loculation as determined radiographically and/or ultrasonographically or a biomarker that predisposes to loculation, such as pH of, or glucose level in, the pleural fluid and/or the presence of microorganisms in the pleural fluid, to make a clinical decision concerning the state of disease and/or treatment options selected for the subject, wherein (i) if the subject's FP is between 0 and 0.1 AU using the standard curve, the probability of success of IPFT is low and the subject should be treated with an alternative approach;

(ii) if the subject's FP is between 0.1 A.U. and 5 A.U. using the standard curve, it is determined to administer further doses or a higher dose of the drug for effective therapy of the disease or condition; and (iii) if the subject's FP is equal to or greater than 5 A.U. using the standard curve, it is determined that no further dose nor higher dose of the drug is required for effective therapy of the disease or condition.

Preferably the above method is used in a subject in which the disease or condition is empyema, complicated parapneumonic pleural effusion or other forms of loculation such as may occur in association with malignant pleural effusions, pleural effusions associated with collagen vascular diseases or pleural effusions associated with chronic organized hemothorax.

The IPFT agent in the above method is preferably an activator of endogenous PLG selected from the group consisting of tissue plasminogen activator (tPA), urokinase plasminogen activator (uPA).

In the above method, DNA is preferably also bound to the solid phase substrate, the detectable label is preferably fluorescein, preferably bound to the fibrin as fluorescein isothiocyanate (FITC). The solid phase substrate is preferably in the form of polystyrene or other plastic multiwell plate to which the labeled fibrin (and preferably DNA) is bound.

The present invention also provides a kit for measuring the FP of a mammalian subject using the above assay method, which kit comprises:

(a) detectably labeled fibrin, and preferably also DNA, bound to a solid phase substrate,
(b) an activator of PLG, for example, tPA, uPA or streptokinase, preferably tPA or uPA;
(c) reagents necessary for activation of plasminogen to plasmin, and for detection of the detectable label, and, optionally,
(d) instructions for carrying out the assay.

In the kit the detectable label is preferably fluorescein and the solid phase substrate is preferably in the form of a polystyrene or other plastic multiwell plate.

BRIEF DESCRIPTION OF THE DRAWINGS

The patent or application file contains at least one drawing executed in color. Copies of this patent or patent application publication with color drawings will be provided by the Office upon request and payment of the necessary fee.

DESCRIPTION OF THE PREFERRED EMBODIMENTS

The present invention is directed to an assay that serves as a companion assay for precision-based intrapleural fibrinolytic therapy (IPFT). In the past, dosing and dosing intervals have been completely empiric in IPFT as currently practiced; there is no current clinically applied test to predict dosing intervals or outcome in patients with radiographically proven loculation. The present invention provides a simple assay based on measurement of the Fibrinolytic Potential (FP) to address these deficiencies. FP is defined as total fibrinolytic activity in pleural fluid when PAIs are neutralized and endogenous plasminogen (PLG) is activated.

Determination of the FP preferably employs a modified fluorescein isothiocyanate (FITC)-film fibrinolytic assay (see Examples and also Komissarov et al., 2011 (supra), 2013 (supra).

A number of parameters beyond active PAI-1 may contribute to the outcome of IPFT including pleural fluid levels of PLG and other proenzymes, serpins and extracellular DNA (Komisarrov et al., 2011, supra). The FP accounts for these variations.

The standard curve for the FPA is preferably generated in the same plate as the patient pleural fluid samples by including a standard amount of a source/precursor of a fibrinolytic substance, preferably PLG in wells containing the detectably labeled fibrin (plus or minus additional DNA) bound to the solid phase. The plasminogen activator is added to these samples in parallel to the patient samples. As noted, a preferred PLG activator is tPA, uPA or streptokinase; more preferably tPA or uPA and the amount of PLG activator added to standards and patient samples is between about 0.1 µg/ml and about 0.5 µg/ml, resulting in a final concentration of between about 2 and 10 nM. As needed, stabilizers, e.g., bovine serum albumin are included. Furthermore, PAI-1 or an anti-plasmin are preferably included in the medium used for the standard curve only, mimicking the presence of such components in the pleural fluid samples.

The FP reflects the net balance between endogenous fibrinolytic enzymes, PLG and inhibitors for a particular subject and can relate IPFT to drug dosing and ultimate outcome.

To additionally monitor changes in the fibrinolytic and plasminogen activator activity with time, approaches described previously are used (Komissarov, A A et al., 2011, supra; Komissarov, A A et al., 2013, supra;

With PAI-1 targeted IPFT the role of PAI-1 independent inactivation of the fibrinolysin increases and primarily controls inactivation of intrapleural PA (See: Komissarov et al., 2013, supra). When the intrapleural PA activity is completely inhibited, inhibition of fibrinolysis and accumulation of newly synthesized endogenous PLG occur, indicating that another dose of IPFT may be given.

Even in the standardized TCN pleural injury model, apparent rate constants for the rate of PAI-1 independent inactivation of uPA is similar, though FP are different An important advantage of the FPA is that it utilizes methods that can ultimately be performed in a community hospital, so that the approach is clinically tractable.

A strong, direct correlation between FP and Gross Loculation Injury Score (GLIS) which is a morphometric pleural injury scoring system (Karandashova et al., supra; Komissarov et al., 2013, supra) is predicted. A GLIS of 0-10 and >10-50 correspond to successful or unsuccessful IPFT, respectively. Such a correlation will consistently be observed in pleural fluids, as seen in treated rabbit models.

The assay is used to determine FP in baseline pleural fluids of patients undergoing IPFT with tPA or scuPA to determine the dose and dose intervals for the particular patient. However, pleural fluids are also collected after IPFT (for example at 4, 8, 12, 18 and 24 h) preferably prior to the next scheduled injection to confirm/reaffirm that intrapleural fibrinolysis is inhibited and endogenous PLG accumulates in the pleural fluid. Inhibition of intrapleural fibrinolysis (fibrinolytic activity is equal to or close to zero) in combination with its increase by 10-100 fold after supplementation of pleural fluid with PLG activator indicates that a subsequent dose of IPFT can be delivered thereafter as needed (e.g., at some time between 6 and 24). Such an inhibition of fibrinolysis was demonstrated by the inventors at 24 h after IPFT in TCN-induced pleural injury in rabbits and in pleural fluids of humans subjected to IPFT with alteplase (the generic name for tPA which is produced as branded drugs Activase® and Cathflo®)

Baseline FP in these animals and after treatment with the PAI-1 targeted IPFT are related to outcomes in that low baseline and post-treatment FP correlate with poor outcome.

The present inventors have for the first time comprehensively studied the intrapleural processing of fibrinolysins to identify mechanism-based strategic approaches to improve outcomes in patients with pleural disease. They comprehensively studied these processes in unique infectious and noninfectious models of pleural injury (Maskell N A et al. *N Engl J Med* 352:865-874, 2005; Corcoran J P et al., *Curr Opin Infect Dis.* 26:196-202, 2013; Karandashova S et al. *Am J Respir Cell Mol Biol:* 48:44-52, 2013) and in human pleural fluids ((Idell, S et al., *Amer Rev Respir Dis* 144:187-194 (1991); Florova, G et al., *Am. J. Respir. Crit. Care Med.* 181:A6824 (2010) and validated active PAI-1 as a therapeutic target and identified promising interventional approaches for PAI-1 targeted PIT for clinical development as they the fundamental pathophysiologic role of PAI-1 in pleural injury.

The FPA is conducted using detectably labeled fibrin bound to a solid phase substrate. Preferably, DNA is also incorporated into the solid phase with the labeled fibrin, to mimic the presence of both fibrin an DNA in pleural fluid of certain patients, such as those with EMP. In one embodiment of the present method, varying concentrations of DNA are bound along with the labeled fibrin to various wells of a multiwell plate, allowing the mimicking of the natural presence of varying amounts of DNA in the pleural fluid across individual EMP patients.

General classes of labels which can be used in the present invention include fluorescent, fluorogenic, chromogenic, or other chemical labels, radioactive isotopes, paramagnetic isotopes. Measurement of any of these types of labels is performed using an appropriate method as is well-known in the art. Common fluorescent labels include fluorescein, rhodamine, dansyl, phycoerythrin, phycocyanin, allophycocyanin, o-phthaldehyde and fluorescamine. A fluorophore, such as the dansyl group, must be excited by light of a particular wavelength to fluoresce. See, for example, Haugland, *Handbook of Fluorescent Probes and Research Chemicals*, Sixth Ed., Molecular Probes, Eugene, Oreg., 1996). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens, are among the most photostable fluorescent labeling reagents known. This group includes the tetramethylrhodamines, X-rhodamines and Texas Red™ derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are the inorganic semiconductor nanocrystals, comprising, for example, cadmium sulfate (Bruchez, M et al., *Science* 281:2013-2016 (1998), and quantum dots, e.g., zinc-sulfide-capped Cd selenide (Chan, W C et al., *Science* 281:2016-2018 (1998)).

A preferred fluorescent label is fluorescein coupled via isothiocyanate (fluorescein isothiocyanate or FITC) to the solid phase fibrin.

A phosphorescent or a chemiluminescent compound can also be coupled to the fibrin. Examples of useful chemiluminescers are luminol, isoluminol, theromatic acridinium ester, imidazole, acridinium salt and oxalate ester. Likewise, a bioluminescent compound may be used to label the fibrin. Bioluminescence is a type of chemiluminescence found in biological systems in which a catalytic protein increases the efficiency of the chemiluminescent reaction. Useful bioluminescent compounds for purposes of labeling are luciferin, luciferase and aequorin.

In yet another embodiment, colorimetric detection is used, based on chromogenic compounds which have, or result in, chromophores with high extinction coefficients.

As noted, the fibrin, or a mixture of fibrin and DNA, is immobilized to a solid supports. For the present compositions and methods, the solid support is preferably any one of polystyrene, polypropylene, polyethylene, dextran, nylon, polyacrylamide, polyvinylidene difluoride, natural cellulose, modified cellulose, nitrocellulose, agarose and magnetic beads. In a preferred embodiment, the surface of polystyrene or other plastic multiwell plates serves as the solid support. Multiwell plates in which the bottoms of the wells comprise nitrocellulose or a similar membrane material and through which liquid can be moved under pressure or vacuum may also be used.

Target validation is supported by the present inventors' and colleagues' recent work directly linking PAI-1 activity to the outcome of pleural injury (Kandrashova et al. supra; Tucker, T et al., *Semin. Thromb. Hemost.* 39:373-381. (2013)). By targeting PAI-1, the needed dose of intrapleural fibrinolysin was reduced by about 8-fold and pathophysiologic extravascular fibrin in loculated fibrinous adhesions was shown to be perpetuated by overexpression of PAI-1 activity, which is otherwise strongly implicated in the pathogenesis of pleural organization and loculation, impaired pleural drainage and outcomes (Idell, S. 2008. *Curr. Opin. Pulm. Med.* 14:310-315 (2008); Chapman, H A. *J. Clin. Invest.* 113:148-157 (2004); Idell, S., *Crit Care Med.* 31:S213-S220 (2003)). These findings parallel the effects of PAI-1 on acute lung injury (ALI) and repair (Idell, S et al., *J Clin Invest* 84:695-705 (1989); Bertozzi, P et al., *New Engl J Med* 322:890-897 (1990)) where PAI-1 increments in airway fluids characterize virtually all forms of ALI (Idell, S et al., *Amer Rev Resp Dis* 136:124-133 (1987); Idell, S et al. *Amer J Physiol* 261:L240-L248 (1991), represent a biomarker of poor outcome (Prabhakaran, P et al., *Am. J Physiol Lung Cell Mol. Physiol* 285:L20-L28 (2003) and promote accelerated lung organization after ALI (Idell, S. et al., *Amer J Path* 135:387-399 (1989); Idell, S. et al., *J Clin Invest* 84:181-193 (1989); Idell, S et al., *Amer J Physiol* 261:L240-L248 (1991); Idell, S. et al., 1989 *Exp Lung Res* 15:739-753 (1989); Eitzman, D T et al. *J. Clin Invest* 95:2416-2420 (1995); Barazzone, C et al. *J. Clin Invest* 98:2666-2673 (1996); Midde, K K et al., *Shock* 36:128-37 (2011))

The FPA measures the total fibrinolytic activity in pleural fluid when, for example, inhibitors of plasminogen activators are neutralized and endogenous PLG is activated.

To perform the FPA, baseline pleural fluid fibrinolytic activity is determined, then PA is added to neutralize PAI-1 and activate PLG. A FITC-fibrin film is formed (with or without incorporated DNA) at the bottom of a 96-well plate as described in Komissarov et al., JBC, 2011, supra). In this assay format, fibrinolysis is monitored by increased fluorescence emission at 510 nm (excitation 490 nm). While a number of parameters beyond active PAI-1 could contribute to the outcome of IPFT, including different levels of PLG, other proenzymes, enzymes, serpins, or extracellular DNA; the FPA is a "snapshot" that accounts for the effects of all of these variables. It reflects the net fibrinolytic balance in a personalized way, which is unique for each subject.

The FPA is measured in baseline pleural fluids and results are tested for correlation with known GLIS scores. With a strong ($r>0.8$) correlation between the FPA and outcomes of IPFT, the assay is validated retrospectively. In a nonlimiting example of validating the FPA prospectively, a set of unmarked samples of baseline pleural fluids (n=30) are analyzed in an operator blinded manner, after which the outcomes for different PAI-1 IPFTs treatments are projected from the FPA results, and compared with actual outcomes (GLIS). The optimal form of PAI-1 targeted IPFT is used and compared to controls treated with fibrinolysin alone, which is ineffective or fibrinolysin alone at 2 mg/kg, the known minimal effective dose. The assay is validated if the outcomes of IPFT predicted by the FPA are successful (GLIS<10) in 5 of 6 rabbits/group or better.

The ability to better target PAI-1 in view of the capability of the present invention in the identification of subjects, predict responses and adjust dose levels, dosing schedules, etc., has implications beyond pleural injury.

According to the present invention, intrapleural targeting of PAI-1 improves IPFT outcomes in EMP in a safe manner, mitigating bleeding risk by using relatively low, otherwise ineffective, doses of fibrinolysin. The present invention serves as a companion test of baseline pleural fluid, the FPA which predicts responses to IPFT, including that which is targeted to PAI-1.

The preferred animal subject of the present invention is a mammal. The invention is particularly useful for human subjects, particularly those suffering from EMP. However, it is also believed to be useful for other diseases of conditions, as noted above, including lung cancer, where IPFT is indicated. By the term "therapy" or "treating" is intended the administering to subjects of a pharmaceutical composition for treatment of any condition requiring IPFT which are discussed herein. Pharmaceutical formulations for use in conjunction with the invention may be formulated for enteral, parenteral, topical administration, but primarily and preferably for intrapleural administration; all these types of formulation may be used concurrently or in a combined regiment to achieve the desired effective delivery and effect of the active ingredient.

Aerosolized solutions may be used for lung instillation of drugs. In a sprayable aerosol preparation, the active drug may be combined with a solid or liquid inert carrier material.

This may also be packaged in a squeeze bottle or in admixture with a pressurized volatile, normally gaseous propellant. The aerosol preparations can contain solvents, buffers, surfactants, and antioxidants.

Having now generally described the invention, the same will be more readily understood through reference to the following examples which are provided by way of illustration, and are not intended to be limiting of the present invention, unless specified.

Example I

Fibrinolytic Potential (FP) Assay

A FITC-fibrin film in a fluorescence quench and dequench assay Wu, J H et al. *Thromb. Haemost.* 74:711-17, 1995) was employed. FITC fibrin plates were prepared described previously (Komissarov et al., *J. Biol. Chem.* 2011, supra). FITC fibrinogen (FITC-Fbg; 3 moles of fluorescein per mole of Fbg), were purchased from Molecular Innovations (Novi, Mich.). FITC-fibrin and FITC-fibrin/DNA (oligonucleotide) films were formed at the bottom of 96-well plates. FITC-Fbg was diluted 1:1 with unlabeled Fbg at a total concentration of 0.4 mg/ml in 0.05 M Hepes/NaOH (pH 7.4, 20 mM NaCl, 5 mM $CaCl_2$) buffer at room temperature. A solution of FITC-Fbg, with or without dsDNA (0-25 g/ml) or oligo(dT)$_{65}$ (0-9.5 M) was titrated into 96-well plates (50 µl/well). Thrombin (final concentration 10 nM) was added to each well. Polymerization of Fbg was confirmed by monitoring the quenching of FITC-fluorescence emission, with time, using a Varian Eclipse. Plates were dried overnight at room temperature, in a dark, enclosed space, washed 3× with 0.3 mL Hepes/NaOH buffer, and were either used immediately or stored at −20° C. Incorporation of the dsDNA and oligonucleotide into the fibrin network was verified by monitoring their increasing levels in the solution during the cleavage of the film by plasmin.

Fibrinolytic activity (FA) is determined by analysis of time changes in the fluorescence emission at 510-520 nm (excitation 480-495 nm) due to dequenching, as described by Wu et al., supra.

Pleural fluid samples (2-100 µl) diluted (2-100 fold) in water or buffer (phosphate buffer or HEPES, 10-500 mM, pH 6.0-8.0, with or without bovine or human serum albumin (BSA or HSA) 1 mg/ml) were added to the wells of the preformed FITC-fibrin plate with or without DNA (0-10%). Extracellular DNA is a part of infectious pleural fluids and the present inventors showed that it affects fibrinolysis, Komissarov et al., 2011, supra). Therefore, inclusion of DNA as a part of the FITC-fibrin matrix allows better simulation of fibrinolysis under conditions when fibrin net is formed in the presence of different levels of endogenous extracellular DNA. According to the present invention, the level of DNA in pleural fluid and, thus, incorporated in fibrin structure, affects IPFT. The rate of degradation of a solid FITC-fibrin film by plasmin depends on different parameters (Wu et al., supra) Assuming that the rate of fibrinolysis is proportional to the concentration of active plasmin, which forms due to the activation of Glu-Plg by tPA and uPA, the slopes of a linear increase in FITC-fluorescence emission on square of time are used for comparison of the rates of fibrinolysis.

FA is measured with or without supplementation of the pleural fluid with corresponding fibrinolysin (0.5-50 nM of tPA or uPA with or without a therapeutic adjunct, such as an antibody or a peptide that mediates or neutralizes inhibitory activities in the pleural space).

The FP is be calculated as a set of differences of FA in supplemented ($FA(n)_{suppl}$) and non-supplemented ($FA(n)_{non-suppl}$) samples of pleural fluids analyzed under the same conditions using the following formula:

$$(n)[FP(n)=FA(n)_{suppl}-FA(n)_{non\ suppl}].$$

where n refers to a set of conditions.

Additional parameters, including but not limited to, pH, the presence of nucleic acids, primarily extracellular DNA) present in pleural fluids in human/animal empyema, affect the rate of fibrinolysis and are the signature of sepsis, as well as activity/concentration of serpins and $\alpha_2$-macroglobulins which are the major inhibitors. The method may be adjusted by including additional measurements of the inhibitory signature of pleural fluid, in order to (i) select preferred conditions (n), preferred ranges of DNA concentration and presence or absence of fibrinolysins (the current drugs of choice in IPFT. According to the invention, the FP assay predicts efficiency dosing and timing of the fibrolysin (or other drug being used in IPFT). Inclusion or exclusion of the fibrinolysins in/from the assay allows assessment or prediction of the drugs effects.

(ii) adjust the measurable determinants of FP. According to the invention, a number of determinants such as anti-fibrinolytic inhibitory activities, nucleic acids, etc. may additionally be included and their effects measured improving predictive abilities of the FP assay. As an example, a human FP assay is conducted with measurement of the following:

(1) FP with FITC-fibrin film formulated with DNA added at the level at which it FP without DNA;
(2) is found in the particular patient;
(3) pH of pleural fluid. and
(4) the level of endogenous intrapleural PAI-1 activity Controls include known amounts of human/animal plasmin (alone or with addition of pleural fluids) and are analyzed in a manner similar to that for the pleural fluid samples under the same conditions.

Figure 1:
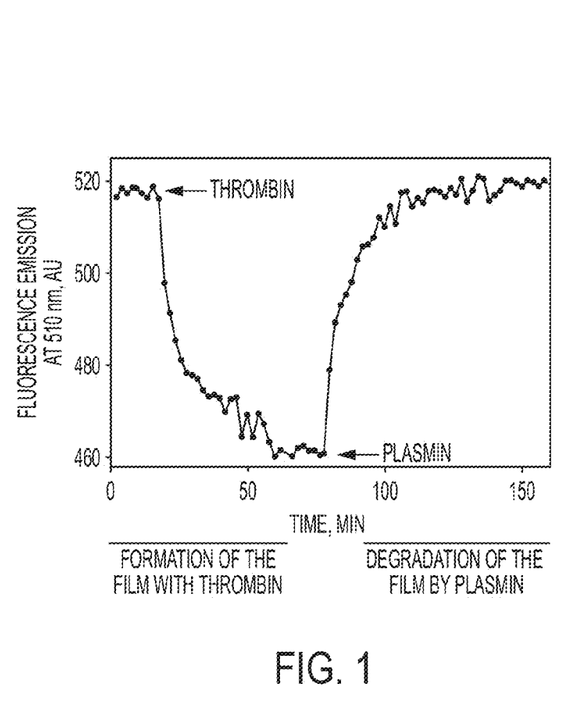
FIG. 1 is a graph showing results of a Fluorescein isothiocyanate (FITC)-Fibrin Film Assay formation and degradation of FITC-fibrin and FITC-fibrin DNA films on a 96 well plate. This assay enables monitoring endogenous Fibrinolytic Activity (FA) in pleural fluids of humans and experimental animals such as rabbits. Fluorescein de-quenching due to digestion of the film by endogenous pleural fluid plasmin approaches saturation when all the FITC-fibrin film is dissolved.
Figure 2:
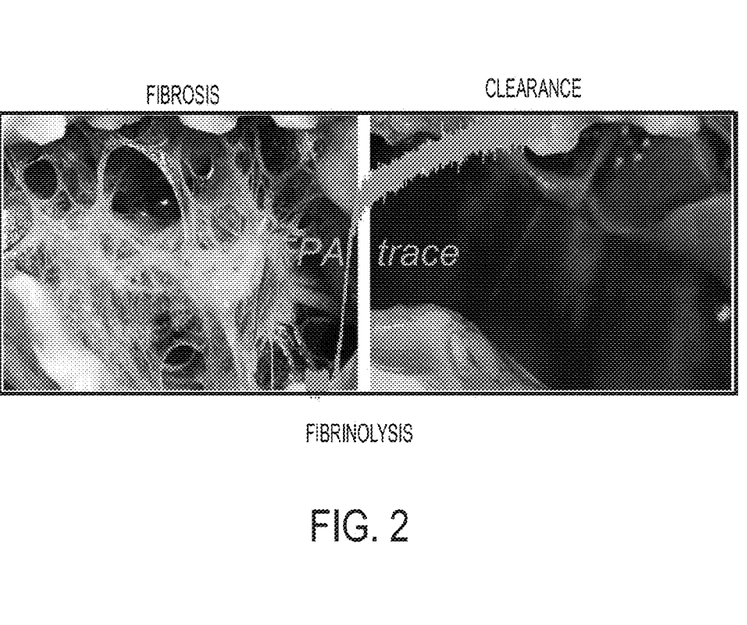
FIG. 2 shows how the FITC-Fibrin Film Assay mimics IPFT such as by treatment with urokinase plasminogen activator (uPA). As in the curve shown in FIG. 1, intrapleural fibrin (Gross Loculation Injury Score or GLIS=50) is digested during successful IPFT resulting in a clear pleural space (GLIS<10). shown on the right. Superimposed over the photographic image of fibrinolysis is the trace of the FITC Fibrin Film Assay of FIG. 1.
Figure 3:
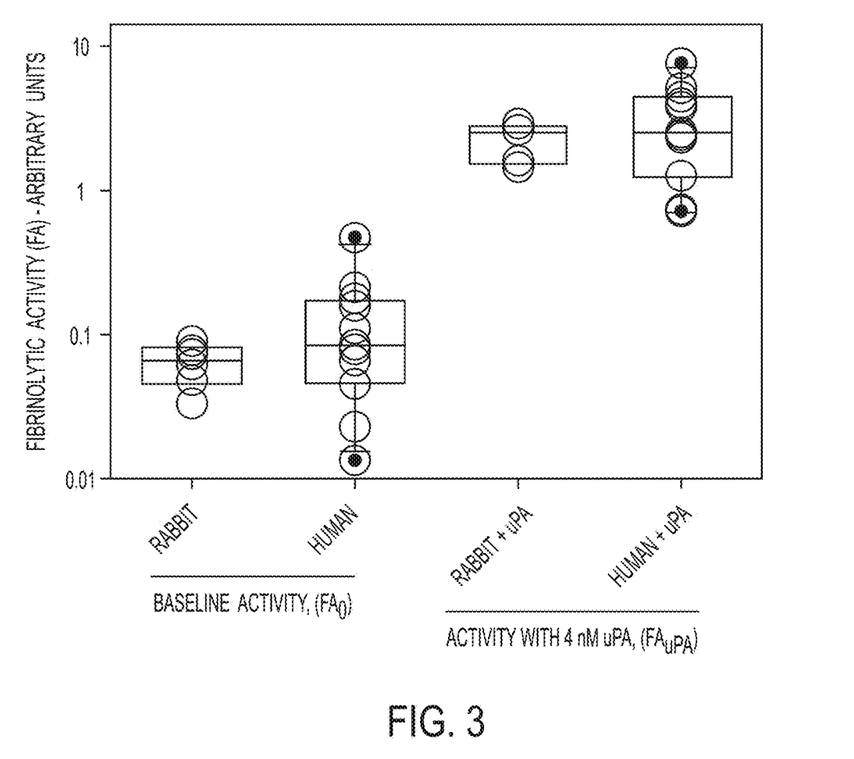
FIG. 3 is a graph showing the results of the FPA in rabbit and human empyema. The graph shows that fibrinolytic activity (FA) on a log scale is/suppressed in human and rabbit empyema. Inhibition FA and PA activities by PAI-1 results in accumulation of PLG in baseline pleural fluids in the human samples and in pleural fluids of rabbits with TCN and EMP-induced injury. The pleural fluids of rabbits were withdrawn prior to IPFT or during drainage, spun down, frozen, and analyzed for FA and FP using a FITC-Fibrin film assay, as described by Komissarov et al., *J. Biol. Chem.* 286:41949-41962 (2011). Supplementation of pleural fluids with uPA, mimicking the effect of IPFT, results in a sharp increase in fibrinolytic activity, indicating the activation of accumulated PLG. The box plot shows the representative baseline fibrinolytic activity in rabbits (n=8) and human patients (n=14) EMP fluids before and after supplementation with 4 nM uPA (or tissue plasminogen activator, tPA, not shown). The human data illustrate the variability (up to 100 fold) of the FA in uPA-supplemented human CPE/EMP baseline pleural fluids. Open circles represent the values in individual rabbits or humans, with the two extreme values emphasized by a dark dot inside the open circle. FP values are calculated by subtracting baseline Fibrinolytic Activity ($FA_0$) from FA after uPA treatment ($FA_{uPA}$). Endogenous FA in the fluids of human patients and animals with empyema was substantially ($p<0.05$) lower than FP. Changes in both FA and FP in the rabbit model were within a narrower range than those observed in humans.

See FIGS. 1-3 for results

FP calibration curves are used to analyze data. These curves were first obtained and validated in rabbit samples (from the present inventors' laboratory) and were transposed and validated with human samples and others; see Example III) and tested in a double-blind manner in samples from animals (inventors' laboratory) and patients (from ongoing clinical trials and from practicing clinicians) who are subjected to IPFT.

The FP assay was initially tested in rabbits (rabbit FPA) and then extended to humans. First, pleural fluids from two rabbit empyema models were compared and, as a control, the rabbit tetracycline model used. With a collection of pleural fluids from animals with known outcome of certain IPFT a relationship between RFP and outcome of IPFT in rabbit empyema is obtained. Other parameters such as levels of DNA, serpin activity, pH, etc. can be added to the RFPA to increase its precision. Then rabbit FPA is validated by analyzing pleural fluids from rabbits with empyema and "prescribing" an IPFT.

In parallel, pleural fluids from humans are analyzed for similarity in molecular signatures with those of the rabbit model. Based on the results shown in FIG. 3, they are similar.

Human FPA is carried out on pleural fluids of patients with known results of IPFT to further establish correlations with the rabbit models. A "customized" FPA is performed on human pleural fluids obtained prior to IPFT which contribute to the selection of the therapy.

According to the invention, the HFPA predicts effective and optimal doses and regimens of the therapeutic intervention for a patient given patient, which results in optimization and commercialization of the human FPA.

In summary, variance in human patients was found to be greater than in animals in the model so that $FA_{suppl}$ and $FA_{non\ suppl}$ and therefore FP may vary up to 100-fold compared to approximately up to 10-fold in the animal model.

As conceived by the present inventors.
(1) pleural fluid is a "personalized footprint" of empyema and its analysis via the present FPA permits evaluation of empyema severity, selection of therapeutic intervention and prediction of the outcome for patients; and
(2) inclusion of parameters other than FP and FA in the FP assay increase its precision.

Example II

Multiloculated Chronic *Streptococcus pneumoniae* Empyema in Rabbits—a Novel Model for Translational Studies Incidence of empyema (EMP), a complication of pneumonia with high mortality rates, increases despite recent advances in modern medicine and vaccination. While there are several acute (3-5 d) models to mimic EMP in pediatric patients, who come to the clinic in 2-6 days, the field of translational research lacks a chronic EMP model, which recapitulates development of multiloculation and significant (>2 mm) pleural thickening. To fill this gap, which slows down understanding molecular mechanisms, which control EMP in humans as well as development of new effective therapeutic and diagnostic approaches, a novel rabbit *S. pneumoniae* chronic EMP model was developed and validated.

EMP was induced by intrapleural injection of $1 \times 10^8$ cfu of *S. pneumoniae*. The course of the disease was monitored by registration of temperature, level of oxygenation, Development of pleural injury was evaluated by ultrasonography and by changes in the lung function. Animals were sacrificed at 1, 2, 3 and 4 weeks and pleural injury was evaluated postmortem. Pleural fluids (PFs) were assessed for levels of active and total plasminogen activator, plasminogen, plasminogen activating and fibrinolytic activity, active α-macroglobulin and extracellular DNA.

Clinical presentation and the time-course in the model closely recapitulated progression human EMP from exudative pleural effusion and loculation to organized multiloculated thorax with atalactic lung. The organized stage of the chronic EMP in rabbits with multiloculation and pleural thickening (>2 mm) were observed by ultrasonography and then directly confirmed by postmortem examination. Pleural fluid analysis revealed elevated total and active PAI-1 resulting in suppression of the fibrinolytic and plasminogen activating activities and accumulation of plasminogen, as well as extracellular DNA to the levels comparable to those observed in PFs of humans with EMP. Supplementation of PF with plasminogen activator resulted in fibrinolytic activity, which varied from animal to animal indicating different Fibrinolytic Potential.

It was concluded that a novel rabbit model of chronic *S. pneumoniae* EMP recapitulates both the time course and the clinical presentation of the human disease including multiloculation and pleural thickening, which are a risk factors for IPFT failure in human EMP, and biochemical signatures characteristic for human EMP. The model provides new opportunities for translational research of the mechanisms controlling EMP development and severity as well as discovering and testing new therapeutic approaches to mitigate EMP in humans.

Example III

Testing and Validation of FPA in Human EMP/CPE Pleural Fluids

FPA is used in baseline EMP or ICPE fluids from patients (Komissarov et al., *J. Biol. Chem.* 2011, supra; Komissarov et al., 2013, supra). Baseline samples are used to compare the baseline FPA in humans, which as indicated above show considerable variability.

Analysis of samples from multicenter trials (Rahman, N M et al., *N. Engl. J. Med.* 365:518-526 2011) showed that while baseline pleural fluid FA activity was greatly suppressed, supplementation with uPA resulted in significant (p<0.001) increases. See FIG. 3. The FPA in baseline human EMP samples varied almost two orders of magnitude, illustrating individual differences, which could affect fibrinolysis and IPFT outcomes.

Human FP predominantly reflects the level of endogenously expressed plasminogen, varies from patient to patient and does not depend on the dose or type of PA used. "Fibrinolytic Potential" is an increase in the level of FA in the pleural fluid under conditions when PAI's are neutralized and all of the endogenous PLG activated.

It was concluded that the FP depends on levels of endogenous plasminogen and inhibitors of fibrinolytic activity in pleural fluid and, thus, reflects the fibrinolytic system of an individual patient. There is less variability in the FP in both rabbit models (TCN-induced injury and empyema) when compared to samples from human patients with empyema. Determination of individual FP, PAI-1 activity, and levels of extracellular DNA prior to and during IPFT are used to guide personalized dosing/dosing intervals for IPFT and thus improve treatment outcomes.

According to the present invention, the Fibrinolytic Potential (FP) is a "molecular footprint" of the efficacy of the fibrinolytic system of an individual and could assist in the assessment of the severity of the pleural injury and in development of personalized IPFT treatments. A strong, direct correlation is found between the FPA results and the clinical and radiologic outcomes in human EMP/complicated pleural effusion CPE samples. (See, e.g., Rahman, N M et al., *N. Engl. J. Med.* 365:518-526 2011).

The references cited above are all incorporated by reference herein in their entirety, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. An assay method for measuring a mammalian subject's fibrinolytic potential (FP) in a sample of pleural fluid of the subject, comprising:
    (a) incubating said pleural fluid sample with detectably labeled fibrin bound to a solid support,
    (b) adding to the sample of (a) an activator of plasminogen (PLG), and (c) adding to separate solid containers to which said labeled fibrin is bound in varying concentrations of
   (i) a fibrinolytic enzyme or
   (ii) PLG and said PLG activator
   and incubating said containers in parallel with, and under the same condition as said sample, to generate a standard curve of FP arbitrary units (FP A.U.) of fibrinolytic activity from which the sample FP value is determined,
wherein the amount of label released per unit time or during a preset time when compared with the standard curve is a measure of said subject's FP.

2. The method of claim 1 wherein DNA is incorporated into the bound, labeled fibrin.

3. The method of claim 1 wherein the detectably labeled fibrin is labeled with a detectable label selected from the group consisting of:
   (a) a fluorescer or fluorogen,
   (b) a chromophore or chromogen,
   (c) a phosphorescer,
   (d) a chemiluminescer,
   (e) a bioluminescer, and
   (f) a radionuclide.

4. The method of claim 3 wherein the fibrin is detectably labeled with the fluorescer fluorescein.

5. The method of claim 1 wherein the solid support is a polymer selected from the group consisting polystyrene, polypropylene, polyethylene, dextran, nylon, polyacrylamide, polyvinylidene difluoride, natural cellulose, modified cellulose, nitrocellulose, and agarose.

6. The method of claim 5 wherein the solid support is in the form of a multiwell plate to which the labeled fibrin is bound.

7. The method of claim 1 wherein the subject is a human.

8. The method of claim 1 wherein, in step (c), the containers comprise said PLG and PLG activator.

9. The method of claim 1 wherein, in step (c), the containers comprise said fibrinolytic enzyme.

10. The method of claim 9 wherein the fibrinolytic enzyme is plasmin.

11. A method of predicting the severity of a pleural disease or condition and treating it by selecting an effective dose or dosing interval with an intrapleural fibrinolytic therapeutic (IPFT) agent in a mammalian subject suffering from a disease or condition in need of the IPFT agent, which method comprises:
   (a) performing the assay method of claim 1 on a pleural fluid sample from the subject to determine the FP of the subject and using the standard curve which is defined over a range of from 0 to 10 FP A.U. of fibrinolytic activity to obtain the subject's FP value, and
   (b) considering the subject's clinical condition, to make a clinical decision concerning the state of disease and/or treatment to be selected for the subject,
   wherein, depending on the FP A.U. values of the standard curve:
      (i) if the subject's FP is between 0 and 0.1 FP A.U., the probability of successful IPFT treatment is low, and a determination that the subject should be treated with an alternative treatment approach is made and the subject treated accordingly; or
      (ii) if the subject's FP is between 0.1 FP A.U. and 5 FP A.U., a determination that further doses or a higher dose of the IFPT agent should be administered for effective treatment of the disease or condition is made and the subject treated accordingly; or
      (iii) if the subject's FP is equal to or greater than 5 FP A.U., a determination that no further dose nor higher dose of the IPFT agent is required for effective treatment of the disease or condition is made and the subject treated accordingly.

12. The method of claim 11 wherein the subject is a human.

13. The method of claim 12 wherein the disease or condition is empyema, complicated parapneumonic pleural effusion, loculation occurring in association with malignant pleural effusion, loculation associated with collagen vascular disease, or loculation associated with chronic organized hemothorax.

14. The method of claim 13 wherein the IPFT agent is an activator of endogenous plasminogen selected from the group consisting of tissue plasminogen activator (tPA) and urokinase plasminogen activator (uPA).

15. The method of claim 11 wherein DNA is incorporated into the fibrin that is bound to said solid support.

16. The method of claim 11 wherein the fibrin is detectably labeled with fluorescein.

17. The method of claim 11 wherein the solid support is in the form of a multiwell plate to which the labeled fibrin is bound.

18. The method of claim 11 wherein, in step (c) of the assay method, the containers comprise said PLG and PLG activator.

19. The method of claim 11 wherein, in step (c), of the assay method, the containers comprise said fibrinolytic enzyme.

20. A kit for measuring the fibrinolytic potential (FP) of a mammalian subject in a sample of pleural fluid of the subject, the kit comprising:
   (a) detectably labeled fibrin, bound to a solid support;
   (b) an activator of plasminogen (PLG);
   (c) reagents for measuring release of detectable label from said labeled, bound fibrin as a measure of fibrinolysis of the labeled fibrin wherein the amount of label released per unit time or during a preset time interval is a measure of said subject's FP,
   (d) separate containers to be incubated in parallel with, and under the same condition as the sample, said containers comprising varying concentrations of
      (i) a fibrinolytic enzyme, or
      (ii) PLG and said PLG activator,
      for generating a standard curve; and,
   (e) instructions for using the kit to determine said FP.

21. The kit of claim 20 further comprising DNA that is incorporated into the fibrin that is bound to said solid support.

22. The kit of claim 20 wherein the detectably labeled fibrin is labeled with a detectable label selected from the group consisting of:
   (a) a fluorescer or fluorogen,
   (b) a chromophore or chromogen,
   (c) a phosphorescer,
   (d) a chemiluminescer,
   (e) a bioluminescer, and
   (f) a radionuclide.

23. The kit of claim 22 wherein the fibrin is detectably labeled with the fluorescer fluorescein.

24. The kit of claim 20 wherein the solid support is a polymer selected from the group consisting of polystyrene, polypropylene, polyethylene, dextran, nylon, polyacrylamide, polyvinylidene difluoride, natural cellulose, modified cellulose, nitrocellulose, and agarose.

25. The kit of claim 24 wherein the solid support is in the form of a multiwell plate to which the labeled fibrin is bound.

26. The kit of claim 20 wherein, in part (d), the containers comprise said PLG and PLG activator.

27. The kit of claim 20 wherein, in part (d), the containers comprise said fibrinolytic enzyme.

28. The kit of claim 27 wherein the fibrinolytic enzyme is plasmin.

29. The kit of claim 20 for, a method comprising
(A) predicting the severity of a pleural disease or condition in the subject based on the subject's determined FP and/or
(B) selecting an effective dose of, or dosing interval for, an intrapleural fibrinolytic therapeutic (IPFT) agent in said mammalian subject that is suffering from a disease or condition in need of treatment with the IPFT agent, which kit comprises
(a) instructions for predicting said severity of said pleural disease or condition and for selection of said effective doses or dosing interval based on determining the subject's FP;
(b) reagents for obtaining a standard curve defined over a range of from 0 to 10 FP arbitrary units (FP A.U.) of fibrinolytic activity, and
(c) reagents and instructions for comparing the FP of the subject to the standard curve, while considering the subject's clinical condition, to make a clinical decision concerning the state of the disease or condition and/or further treatment methods selected for the subject, wherein the method of using the kit yields the following determinations:
(i) for a range of low FP values between 0 and 0.1 FP A.U., the probability of success of intrapleural fibrinolytic therapy is low and the subject should be treated with an alternative treatment approach;
(ii) for an range of intermediate FP values between 0.1 FP A.U. and 5 FP A.U., further doses or a higher dose of the IPFT agent should be administered for effective treatment of the disease or condition; and
(iii) for a range of high FP values that are equal to or greater than 5 FP A.U., the disease or condition has been treated effectively so no further dose nor higher dose of the IPFT agent is required.

30. The kit of claim 29 further comprising DNA that is incorporated into the fibrin that is bound to the solid support.

31. The kit of claim 29 wherein the IPFT agent is an activator of endogenous tissue plasminogen activator (tPA) or urokinase plasminogen activator (uPA).

32. The kit of claim 29 wherein the detectable label is fluorescein.

33. The kit of claim 29 wherein the solid support is in the form of a multiwell plate to which the labeled fibrin is bound, and said separate containers are wells of said plate.

34. The kit of claim 29 wherein the kit and its instructions are directed to treatment of a disease or condition selected from the group consisting of empyema, complicated parapneumonic pleural effusion, loculation occurring in association with malignant pleural effusion, loculation associated with collagen vascular disease, and loculation associated with chronic organized hemothorax.

* * * * *

UNITED STATES PATENT AND TRADEMARK OFFICE
CERTIFICATE OF CORRECTION

PATENT NO. : 10,175,255 B2
APPLICATION NO. : 15/086623
DATED : January 8, 2019
INVENTOR(S) : Andrey A. Komissarov et al.

Page 1 of 1

It is certified that error appears in the above-identified patent and that said Letters Patent is hereby corrected as shown below:

In the Specification

Column 1, Lines 10-14, "STATEMENT OF RIGHTS TO INVENTIONS MADE UNDER FEDERALLY SPONSORED RESEARCH" delete the following paragraph:
"This invention was funded in part by grants NIH P50 107186 (CADET 1) and CADET II:1UH2HL123585-01. from the National Heart, Lung and Blood Institute , National Institutes of Health, which provides to the United States government certain rights in this invention."

Add the following paragraph:
-- This invention was made with government support (NIH HL107186) awarded by the National Institutes of Health. The government has certain rights in the invention. --

Signed and Sealed this
Twenty-sixth Day of March, 2019

Andrei Iancu
*Director of the United States Patent and Trademark Office*